US009764088B2

(12) United States Patent
Huculak et al.

(10) Patent No.: US 9,764,088 B2
(45) Date of Patent: Sep. 19, 2017

(54) GAS SYRINGE FILLING DEVICE AND METHODS FOR MAKING AND USING THEM

(71) Applicant: ALTAVIZ, LLC, Irvine, CA (US)

(72) Inventors: John C. Huculak, Mission Viejo, CA (US); Jack R. Auld, Laguna Niguel, CA (US); Christopher L. McCollam, Irvine, CA (US); James Lescoulie, Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 0 days.

(21) Appl. No.: 14/269,062

(22) Filed: May 2, 2014

(65) Prior Publication Data

US 2014/0330204 A1    Nov. 6, 2014

Related U.S. Application Data

(60) Provisional application No. 61/819,452, filed on May 3, 2013.

(51) Int. Cl.
*A61M 37/00* (2006.01)
*A61M 5/178* (2006.01)
*A61M 5/20* (2006.01)

(52) U.S. Cl.
CPC ........ *A61M 5/1782* (2013.01); *A61M 5/2046* (2013.01); *A61M 2207/00* (2013.01); *Y10T 29/49826* (2015.01)

(58) Field of Classification Search
CPC .............. A61M 5/1782; A61M 5/2046; A61M 2005/006; A61M 13/00; A61M 13/003; A61M 2202/02

(Continued)

(56) References Cited

U.S. PATENT DOCUMENTS 3,853,157 A * 12/1974 Madaio ............... A61M 5/1782
                                                                141/2
5,019,037 A     5/1991 Wang et al.
(Continued)

FOREIGN PATENT DOCUMENTS

DE         2543284 A1    3/1977
WO    2005115529 A2    12/2005

OTHER PUBLICATIONS

International Search Report and Written Opinion dated Sep. 5, 2014 in PCT International Application No. PCT/US2014/036706 filed May 2, 2014, (26 pages).

(Continued)

*Primary Examiner* — Kevin C Sirmons
*Assistant Examiner* — Leah Swanson
(74) *Attorney, Agent, or Firm* — William A. English; Vista IP Law Group LLP (57) ABSTRACT

Systems and methods are provided for filling syringes, e.g., for use during pneumatic retinopexy or other medical procedures. In one embodiment, the system includes a housing carrying a gas canister including an outlet communicating with a fluid path extending from the outlet to a syringe cavity. A syringe includes a barrel receivable in the syringe cavity such that a port of the barrel communicates with the fluid path. An actuator is provided on the housing for selectively opening the outlet of the gas canister to deliver gas therein along the fluid path into the interior of the barrel, thereby causing the plunger to move from a distal position to a proximal position.

29 Claims, 7 Drawing Sheets

(58) Field of Classification Search
USPC .......................................... 604/26, 143, 147
See application file for complete search history.

(56) References Cited

U.S. PATENT DOCUMENTS

| | | | |
|---|---|---|---|
| 5,334,163 A | | 8/1994 | Sinnett et al. |
| 5,336,175 A | * | 8/1994 | Mames ................ A61K 9/0048 128/898 |
| 5,620,422 A | * | 4/1997 | Halbich .............. A61M 5/1782 141/27 |
| 6,254,575 B1 | * | 7/2001 | Thorne, Jr. ......... A61M 5/1782 128/919 |
| 6,439,276 B1 | * | 8/2002 | Wood ................. A61M 5/1782 141/27 |
| 6,599,280 B1 | | 7/2003 | Pynson et al. |
| 2002/0189705 A1 | | 12/2002 | Reihl et al. |
| 2006/0089594 A1 | | 4/2006 | Landau |
| 2008/0208114 A1 | | 8/2008 | Landau et al. |
| 2010/0042071 A1 | | 2/2010 | Reynolds et al. |
| 2013/0204130 A1 | | 8/2013 | McArthur et al. |

OTHER PUBLICATIONS

European Patent Office, Search Report and Response for European Patent Application No. EP14791389, Applicant: Altaviz, LLC; 30 pages.

* cited by examiner

GAS SYRINGE FILLING DEVICE AND METHODS FOR MAKING AND USING THEM

RELATED APPLICATION DATA

This application claims benefit of provisional application Ser. No. 61/819,452, filed May 3, 2013, the entire disclosure of which is expressly incorporated by reference herein.

FIELD OF THE INVENTION

The present invention relates to gas syringe filling devices and to methods for making and using such devices, and to systems including gas syringe filling devices and syringes, and to methods for making and using such systems.

BACKGROUND

Retinal detachment is a disorder of the eye in which the retina separates from its underlying layer of support tissue. Initial detachment may be localized, but without prompt treatment, the entire retina may detach, leading to vision loss and eventually blindness.

The retina is a thin layer of light sensitive tissue on the back wall of the eye. The optical system of the eye (cornea and lens) focuses light on the retina similar to the way light is focused on the film of a camera. The retinal tissue translates the focused image into neural impulses and sends them to the brain via the optic nerve. Occasionally, Posterior Vitreous Detachment (PVD), injury or trauma to the eye or head, or other conditions may cause a small tear in the retina. The tear allows vitreous fluid to seep through and collect under the retina, lifting the retina, and allowing it to peel away or otherwise separate from the underlying tissue.

There are several methods for treating a detached retina, which involve finding and closing any breaks that have formed in the retina. For example, pneumatic retinopexy is a procedure, which may be performed in a physician's office or operating room, e.g., under local anesthesia. A gas bubble is injected into the eye after which laser photocoagulation or cryopexy treatment may be applied to the retinal hole, break, or tear. The patient's head is then positioned so that the bubble rests against the retinal tear. Patients may keep their heads tilted or lie face down, e.g., for several days or other period of time, to keep the gas bubble in contact with the retinal tear. Surface tension of the gas/water interface may seal the tear in the retina, and allow the retinal pigment epithelium (RPE) to pump the subretinal space dry and draw the retina back into place.

Generally, pneumatic retinopexy involves the use of a one or three milliliter (1 or 3 ml) syringe typically filled with 0.3 to 0.6 ml of expansile gas and using a small gauge needle, e.g., 30 gauge or smaller. The syringe may be manually filled with gas transferred from a reusable pressurized gas canister containing one of a number of expansile gases, e.g., $SF_6$, $C_3F_8$, or $C_2F_6$. The gas canister has a reusable pressure regulator, e.g., set to 10 psi, to reduce the pressure of the gas in the gas canister before being discharged into the syringe. A 0.22 micron or smaller filter is typically used to ensure the gas transferred to the syringe is free of contaminants.

With the syringe plunger fully depressed, a filter is connected to the distal end of the syringe, and the syringe-filter assembly is subsequently connected to the regulator attached to the gas canister. Typically, the syringe includes a male luer fitting and the filter includes male and female luer fittings on either end, with the female fitting connected to the syringe's male fitting, leaving a male fitting to the connect to the regulator. Typically, the regulator also includes a male luer fitting, and so a female-to-male luer adapter is generally used to make the connection between the filter and the regulator. Given the multiple connections typically involved, there is some risk of the pressurized gas escaping and/or air leaking into the system and into the syringe, thereby reducing the effectiveness of the gas delivered using the syringe.

Once the necessary connections are made, a valve of the gas canister is opened to release gas to the regulator and a valve on the regulator is opened to release regulated gas to the connected syringe-filter assembly, i.e., into the interior of the syringe. Generally, with the syringe plunger fully depressed, the regulated gas may be drawn into the syringe, e.g., based on the pressure of the regulated gas and/or manual retraction of the plunger. For example, the pressure of the gas may be sufficient to push the plunger back automatically during the filling process and fill the interior of the syringe with gas.

However, with many small diameter syringes, the regulated pressure (e.g., 10 psi) may not be enough pressure to push the plunger, e.g., due to the relatively high friction between the plunger and syringe wall and/or the small surface area of the piston contacted by the regulated gas, and so the clinician may need to pull on the plunger to complete the filling process. One of the risks of this action is that the clinician may pull too quickly, which may draw room air into the syringe, e.g., through the many connections, reducing the concentration of the gas (from 100%), thereby reducing the effectiveness of the gas tamponade provided when the gas is injected into a patient's eye.

To address this problem (since the pressure regulator is typically not adjustable and fixed at 10 psi), it has been suggested to fill a larger, e.g., 60 ml, syringe from the gas canister. Given the larger surface area of the plunger in such larger syringes, the regulated pressure may be sufficient to push the plunger and fill the larger syringe. Once filled, the larger syringe may then disconnected from the regulator (after closing the valve(s) of the gas canister and/or regulator) and connected to the smaller (e.g., 1 or 3 ml) syringe-filter assembly described above, e.g., using a female-to-female adaptor. The plunger of the larger syringe is then depressed to eject the gas therein and create sufficient pressure to push the plunger of the smaller syringe and fill the smaller syringe, thereby transferring the gas from the larger syringe to the smaller syringe for use during a procedure. Thus, this filling procedure may require multiple steps, which may increase the length of the time of the procedure and/or risk leakage of the pressurized gas and/or introduction of air into the syringe.

After filling the 1 or 3 ml syringe (whether from a larger syringe or directly from the gas canister and regulator), the filter is disconnected from the syringe and a needle is connected to the syringe, e.g., a 30 gauge or other relatively small gauge needle with a female luer fitting. The syringe is then ready to be used during a medical procedure, e.g., a pneumatic retinopexy procedure.

Upon completion of the procedure, single-use items, e.g., the syringe, needle, and filter, are disposed of, and reusable items, e.g., the gas canister and its pressure regulator, are closed and stored for future use. For example, the regulator is closed after filling the larger syringe or the smaller syringe (if filled directly from the gas canister), and the gas canister is closed to prevent gas leakage during storage and/or between procedures. Thus, one of the additional risks of conventional systems and methods is that the clinician or other user may forget to close the valve(s) of the regulator and/or gas canister or may not fully close the valve(s), thereby releasing pressurized gas from the gas cylinder. Such loss may increase the cost of future procedures since additional cylinders of gas will be needed, and/or may potentially release harmful greenhouse gases into the atmosphere. Further, if the gas cylinder is drained unexpectedly while in storage, the lack of pressurized gas may not be discovered until immediately before another procedure, which may disrupt patient flow and/or treatment while additional gas cylinders are obtained.

Accordingly, devices for loading syringes and/or performing retinal repair procedures would be useful.

SUMMARY

The present invention is directed to gas syringe filling devices and to methods for making and using such devices. In addition, the present invention is directed to systems including gas filling devices and syringes, and to methods for making and using such systems, e.g., to perform retinal repair, such as pneumatic retinopexy, and/or other medical procedures.

In accordance with one embodiment, a system is provided for performing a medical procedure that includes a housing carrying a source of pressurized gas including an outlet communicating with a fluid path; and a syringe comprising a barrel including a port communicating with an interior of the barrel and a plunger slidable within the interior of the barrel, the syringe at least partially receivable in a cavity in the housing such that the port communicates with the fluid path. A latch or other feature may be provided for releasably securing the barrel in the cavity, and an actuator may be provided for selectively opening the outlet of the source of pressurized gas and/or otherwise delivering gas therein along the fluid path into the interior of the barrel, thereby causing the plunger to move from a distal position to a proximal position. Optionally, the latch may include a catch for limiting movement of the plunger beyond the proximal position. In addition or alternatively, one or more components may be included in the fluid path, e.g., one or more actuation pins, filters, pressure relief features or controllers, and the like.

In accordance with another embodiment, a gas syringe filling device is provided that includes a housing defining a fluid path communicating with a cavity sized for receiving at least a portion of a syringe therein; a source of pressurized gas within the housing comprising an outlet communicating with the fluid path; and an actuator for selectively delivering gas therein along the fluid path into a barrel of a syringe received in the cavity.

In accordance with still another embodiment, a method is provided for making a gas syringe filling device that includes providing a source of pressurized gas; forming a housing defining a recess for receiving the source of pressurized gas, cavity for receiving at least a portion of a syringe, and a fluid path therebetween; and providing a latch on the housing adjacent the cavity configured to releasably secure a syringe within the cavity. Optionally, a syringe may be inserted into the cavity and the latch may secure the syringe relative to the housing.

In accordance with yet another embodiment, a method is provided for performing a medical procedure that includes providing a housing including a source of pressurized gas, a fluid path communicating with an outlet of the source of pressurized gas, and a syringe comprising a barrel at least partially positioned in a cavity of the housing such that a port communicating with an interior of the barrel is in communication with the fluid path. The outlet of the source of pressurized gas may be opened or otherwise actuated to deliver gas from the source of pressurized gas along the fluid path into the interior of the barrel, thereby causing the plunger to move from a distal position to a proximal position. The barrel may be removed from the housing, and the syringe may be used to deliver pressurized gas to a patient.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which.

DETAILED DESCRIPTION OF THE EXEMPLARY EMBODIMENTS

Figure 1:
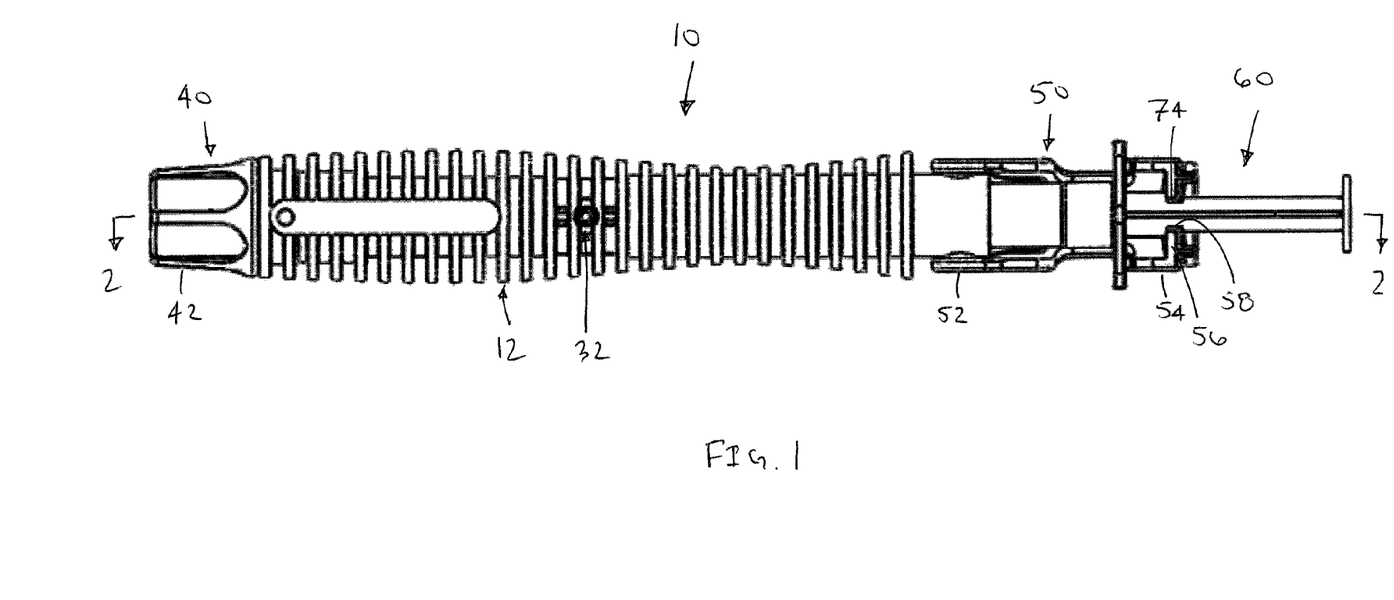
FIG. 1 is a top view of an exemplary embodiment of a gas syringe filling device including a syringe received within a cavity of the device.
Figure 2:
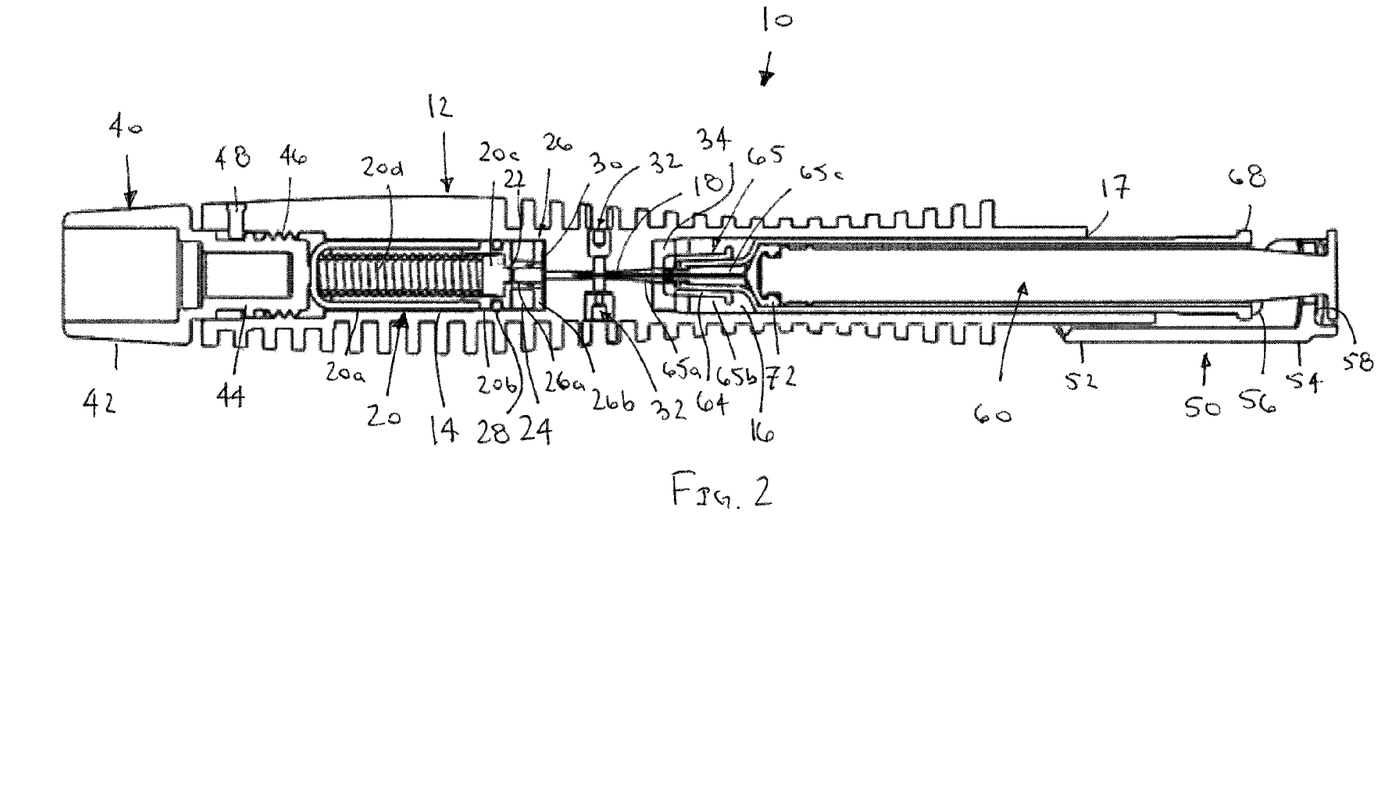
FIG. 2 is a cross-sectional side view of the device of FIG. 1 taken along line 2-2.

Turning to the drawings, FIGS. 1 and 2 show an exemplary embodiment of a pneumatic filling device 10 for filling a syringe 60. Generally, the device 10 includes a housing 12 defining a recess 14 for a source of pressurized gas, e.g., a gas cylinder or canister 20, a cavity 16 for receiving at least a portion of the syringe 60, and a fluid path 18 communicating between the gas canister 20 and a syringe 60 received in the cavity 16, as described further elsewhere herein. Optionally, the housing 12 may include one or more additional components, e.g., within the recess 14 and/or along the fluid path 18, such as one or more filters (e.g., one filter 30 shown), pressure regulators or controllers (e.g., a pair of relief valves 32 shown), seals 28, 34, actuators 40, biasing mechanisms 24, actuation pins or puncturing elements (e.g., actuation pin 26 shown), and the like.

The housing 12 may integrate the components substantially permanently therein, e.g., to provide a single-use device that may be used to fill a syringe 60 for a medical procedure, such as a pneumatic retinopexy procedure, which may allow fast and/or convenient filling of the syringe 60 before or during a procedure, as described further elsewhere herein. In addition, the housing 12 may minimize the size and/or length of the fluid path 18, which may reduce dead-air space in the fluid path 18, e.g., to maintain a high level of gas purity and/or reduce the amount of waste gas released during use of the device 10. In addition or alternatively, the housing 12 may be sized and/or configured to be a relatively light-weight hand-held device, optionally, having an outer surface shaped, textured (e.g., including a plurality of annular ribs or other gripping features, as shown in FIG. 1), and/or otherwise contoured to facilitate holding and/or manipulating the device 10, e.g., with one hand.

Figure 6:
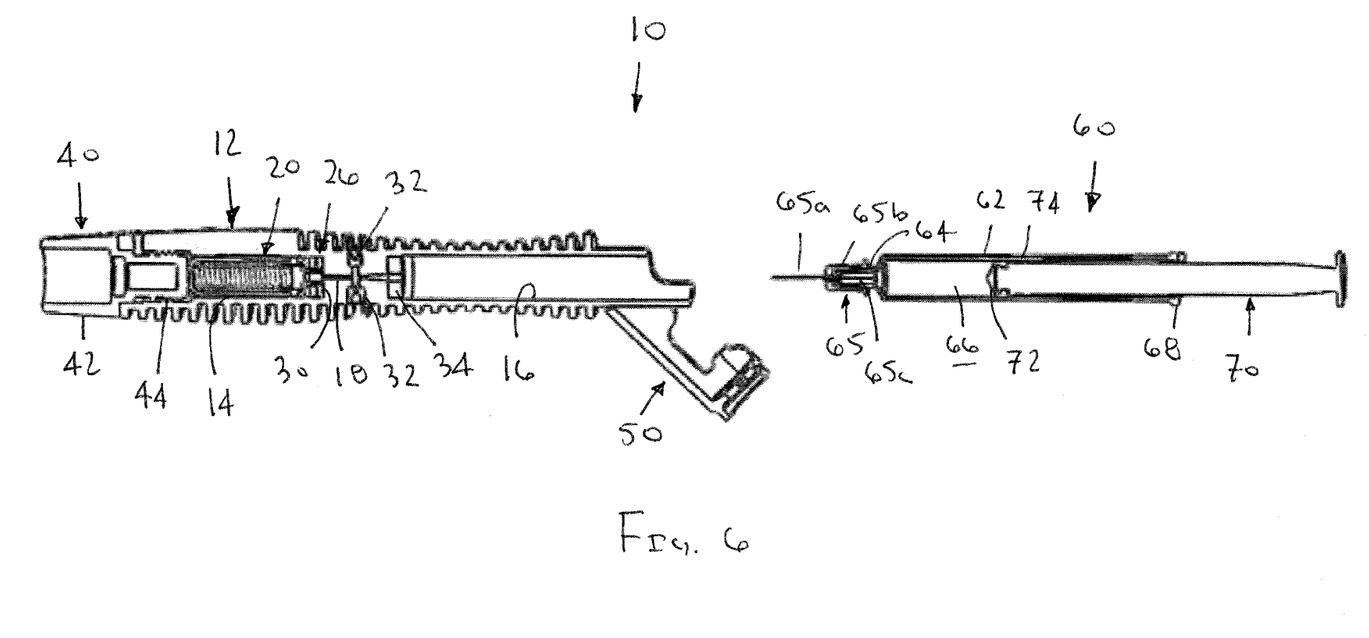
FIG. 6 is a cross-sectional side view of the device of FIGS. 1-5 showing the filled syringe being removed from the device.

In an exemplary embodiment, the syringe 60 may be a conventional syringe, such as those typically used in pneumatic retinopexy procedures. Generally, as best seen in FIGS. 2 and 6, the syringe 60 includes a barrel 62 including a side wall reducing to a distal port 64 communicating with an interior 66 of the barrel 62, e.g., having an interior volume of between about one and three milliliters (1-3 ml), e.g., about 1-1.5 ml, when filled, and a plunger 70 including a piston 72 slidable within the interior 66 of the barrel 62.

In addition, the syringe 60 may include a needle assembly 65, e.g., removably or permanently attached to the distal port 64 of the barrel 62. In an exemplary embodiment, the needle assembly 65 may include a needle 65a mounted to an insert 65c sized to fit into the port 64. The insert may at least partially fill the interior of the port 64, e.g., to minimize air space that may otherwise allow unwanted air to enter the interior 66 of the barrel 62 during filling. The needle assembly 65 may also include a cap 65b that may be secured over the port 64, e.g., including a female luer fitting that may be threaded over a male luer fitting (not shown) on the port 64. The insert and needle 65a may be permanently attached to the cap 65b, e.g., such that the insert is received in the port 64 and the needle 65a extends distally from the syringe 60 when the cap 65b is connected over the port 64. Alternatively, the needle 65a and insert may be inserted into the port 64 and the cap 65b may be separately attached to the port 64, e.g., to secure the needle 65a relative to the port 64. In a further alternative, a needle may be integrally formed with the barrel, e.g., molded or otherwise substantially permanently integrated with the barrel (not shown). In either embodiment, the needle 65a may be a relatively small gauge needle, e.g., thirty gauge or smaller. In a further alternative, the port 64 may include a connector (e.g., a male luer fitting) and the needle assembly 65 may be omitted, e.g., for subsequent attachment after filling the syringe 60.

The barrel 62 also includes a pair of finger flanges 68, e.g., for use in cooperation with the plunger 70 to advance the piston 72 to inject the gas or other compounds from within the interior 66 of the barrel 62, similar to conventional syringes. In addition, the flanges 68 may interact with a latch 50 on the device 10, e.g., for releasably securing the syringe 60 within the cavity 16, as described further elsewhere herein. Alternatively, other dedicated features (not shown) may be provided on the barrel 62 that may engage corresponding elements on the latch 50 or the housing 12 to releasably secure the syringe 60 within the cavity 16. In addition or alternatively, the plunger 70 may include one or more features, e.g., notch 74, that may interact with one or more corresponding elements on the latch 50, e.g., to limit movement of the plunger 70, also as described further elsewhere herein.

For example, the latch 50 may be pivotally or otherwise movably coupled to the housing 12 adjacent the cavity 16, e.g., adjacent an opening 17 in the housing 12 communicating with the cavity 16 and into which a syringe 60 may be inserted and/or removed. The latch 50 may include one or more detents or other features 56 that engage corresponding features on the syringe 60, e.g., that receive and/or engage the flanges 68. For example, the latch 50 may include a first end 52 coupled to the housing 12 and a second free end 54 such that the latch 50 is pivotable between a disengaged position, e.g. as shown in FIG. 6, and an engaged position, e.g., as shown in FIGS. 1 and 2. As shown, the first end 52 may be connected to the housing 12 by hinge elements (not shown), e.g., tabs on the housing 12 that are received in corresponding recesses or holes on the first end 52 (or vice versa), allowing the latch 50 to pivot about an axis of the hinge elements between the disengaged and engaged positions.

In the disengaged position, the opening 17 in the housing 12 may be exposed allowing the barrel 62 of a syringe 60 to be inserted therethrough into the cavity 16 and/or removed from the cavity 16, as described further elsewhere herein. In the engaged position, the latch 50 may engage features of the fully inserted syringe 60 to secure the syringe 60 within the cavity 16. For example, the second end 54 of the latch 50 may include one or more tabs 56 that snap or otherwise pass over the flanges 68 on the syringe barrel 62, thereby preventing the syringe 60 from being removed from the cavity 16.

In addition, the latch 50 may include a groove 58, e.g., adjacent the tabs 56 that may slidably engage the plunger 70 and/or limit movement of the plunger 70. For example, the plunger 70 may include a notch, a raised element, and/or other feature 74, e.g., adjacent the piston 72, which may engage with the groove 58, e.g., to prevent complete removal of the plunger 70 from the barrel 62 and/or limit motion of the plunger 70 to set a maximum interior volume within the barrel 62 for receiving pressurized gas.

Alternatively, other features (not shown) may be provided on the syringe barrel 62 and housing 12 for releasably securing the syringe 60 in the cavity 16 instead of the latch 50. For example, tabs, recesses, detents or other features may be provided on the outer surface of the barrel 62, which may engage mating features on the housing 12 when the syringe 60 is fully received in the cavity 16. The features may be disengaged by pulling the syringe 60 with sufficient force, e.g., allowing the syringe 60 to be removed from the housing 12 after filling.

Figure 3:
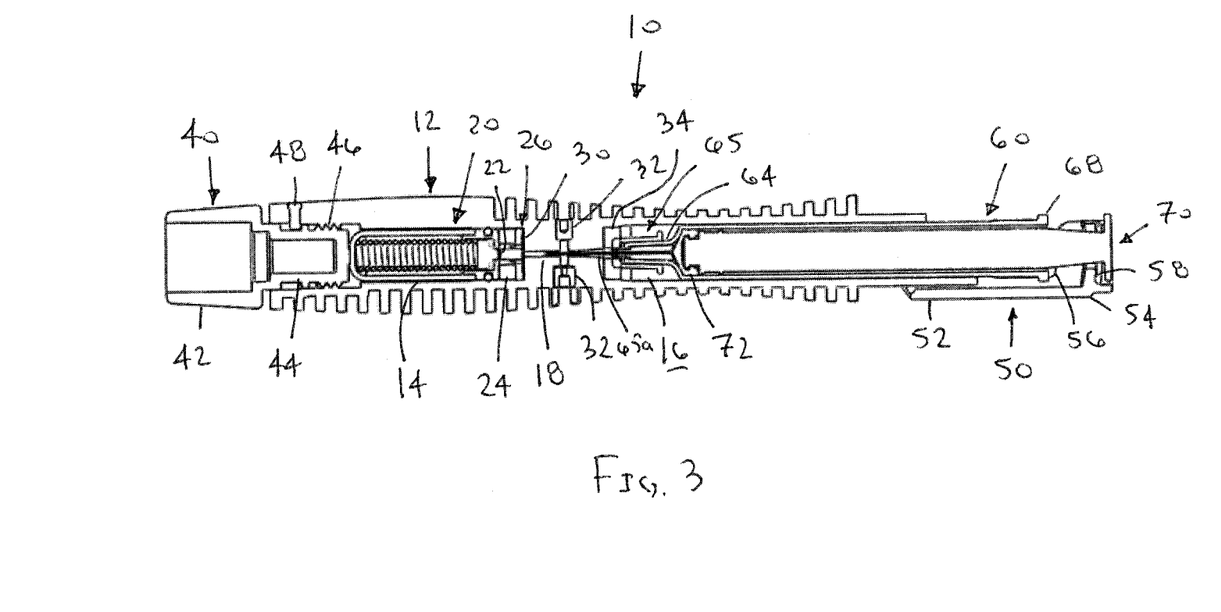
FIGS. 3-4 are cross-sectional side views and FIG. 5 is cross-sectional top view of the device of FIGS. 1 and 2 showing a method for filling the syringe with pressurized gas.
Figure 4:
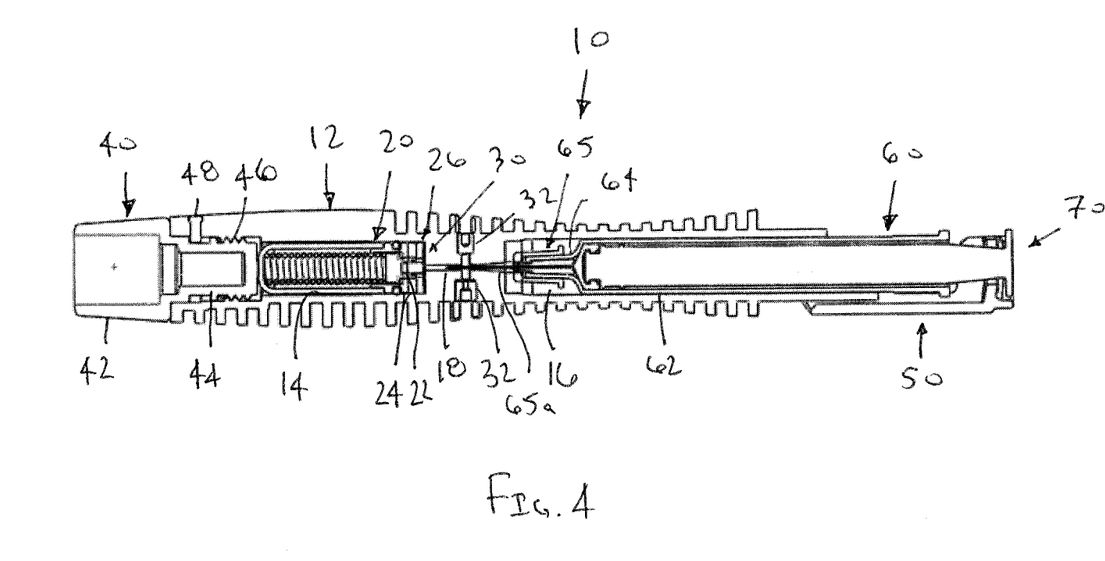
Figure 5:
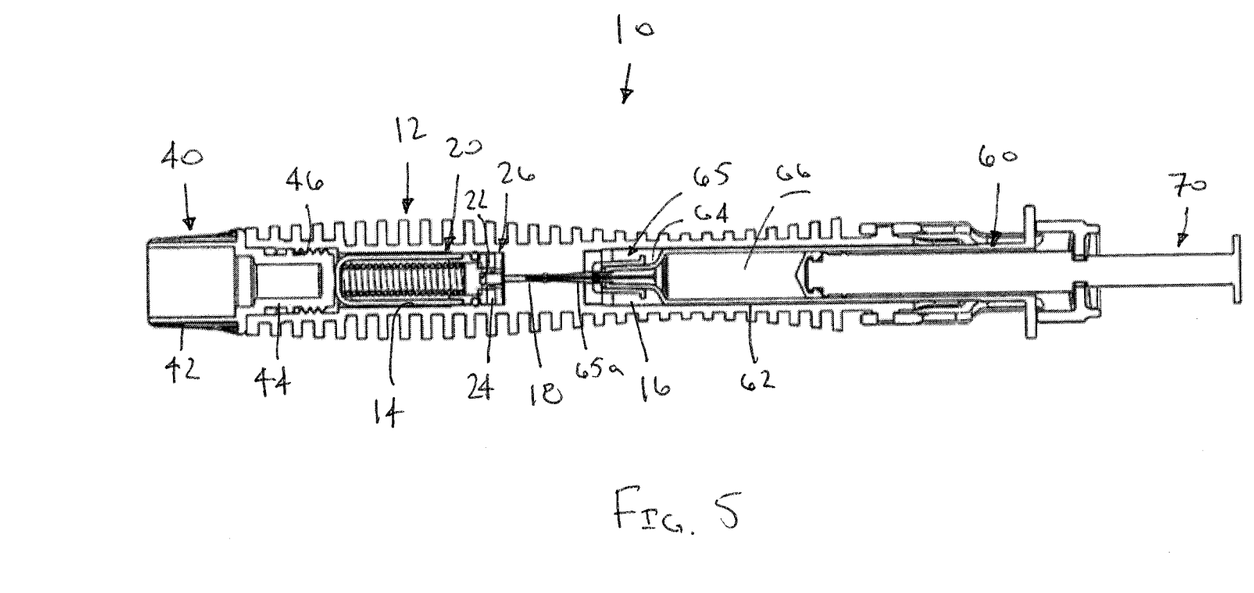

With reference to FIGS. 3-5, the actuator 40 may be mounted on the housing 12 for selectively delivering pressurized gas from the gas canister 20 along the fluid path 18 into the syringe 60. For example, as best seen in FIGS. 3 and 4, the actuator 40 may include a button or cap 42 exposed outside the housing 12 and slidably mounted on the housing 12, e.g., on the end of the housing 12 closest to the recess 14 and a stem 44 that enters the housing 12 and contacts or otherwise engages the gas canister 20 within the recess 14. The gas canister 20 may be movable within the recess 14 between a first position, e.g., as shown in FIG. 3, in which the outlet 22 of the gas canister 20 is spaced away from the fluid path 18, and a second position, e.g., as shown in FIG. 4, in which the outlet 22 is closer to the fluid path 18 and is opened to deliver gas from the gas canister 20.

A bumper or other biasing mechanism 24 may be provided in the recess 14, e.g., around, adjacent, or otherwise coupled to the gas canister 20, that biases the gas canister 20 to the first position (and therefore the actuator 40 to an outer position shown in FIG. 3), yet allows the gas canister 20 to resiliently move to the second position (when the actuator is moved to an inner position shown in FIG. 4). For example, the bumper 24 may be an annular body formed from foam or other resilient material disposed adjacent the outlet 22 of the gas canister 20, e.g., between the gas canister 20 and actuation pin 26. The bumper 24 may be resiliently compressible to allow the gas canister 20 to move between the first and second positions, e.g., compressing between the gas canister 20 and the actuation pin 26 when the gas canister 20 is directed to the second position. Alternatively, one or more springs (not shown) may be provided adjacent the gas canister 20 to bias the gas canister 20 towards the first position.

In an exemplary embodiment, the stem 44 and housing 12 may include cooperating threads 46 that allow the cap 42 to be rotated to cause the stem 44 to be advanced and/or retracted relative to the recess 14, thereby directing the gas canister 20 between the first and second positions and resiliently compressing the bumper 24. A set screw 48 or other element on the housing 12 may limit movement of the actuator 40 and/or prevent removal from the housing 12. Alternatively, the actuator 40 may be directed axially into the housing 12 without rotation, e.g., by simply pressing on the cap 42 to direct the gas canister 20 to the second position, and then releasing the button 42 to automatically direct the gas canister 20 back to the first position, e.g., due to the resilient bias provided by the compressed bumper 24.

In an exemplary embodiment, the source of pressurized gas 20 is a unit-dose gas micro-cylinder, e.g., including sufficient volume of pressurized gas for a single procedure or patient. For example, the gas canister 20 may have an interior volume of between about 0.5 and one milliliter (0.5-1.0 ml), e.g., not more than 1 ml. The gas canister 20 may contain one or more expansile gases, e.g., an ophthalmic gas, such as those used for a pneumatic retinopexy procedure, e.g., $SF_6$, $C_3F_8$, or $C_2F_6$, and the like. The gas contained within the gas canister 20 may be loaded therein under predetermined pressure and/or other conditions, e.g., in a gaseous or liquid form.

Figure 2A:
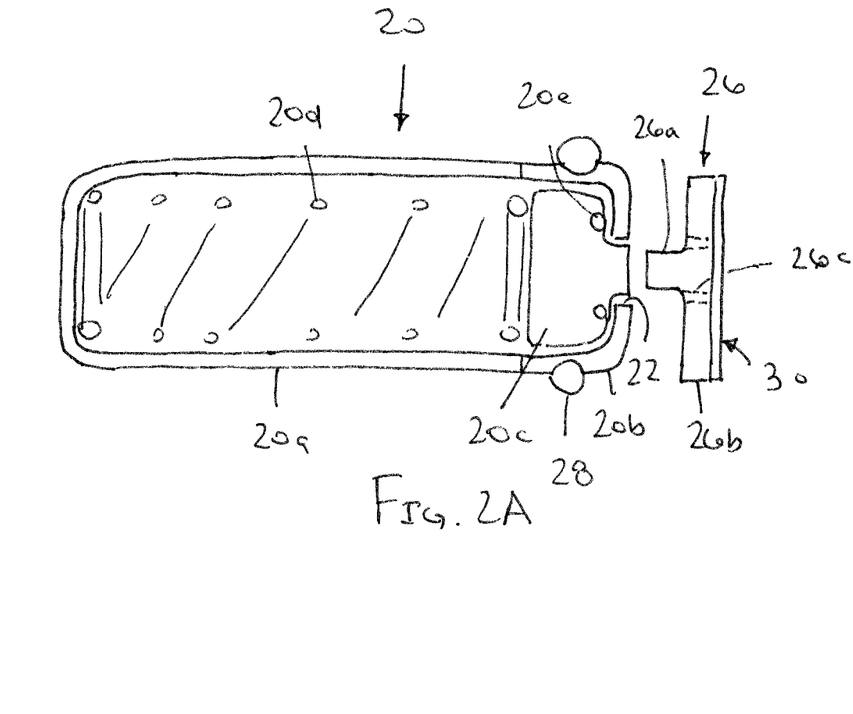
FIG. 2A is a cross-sectional detail of a gas canister and a portion of a fluid path of the device of FIG. 2.

In the embodiment shown in FIG. 2A (where the housing has been omitted for clarity), the gas canister 20 includes a cylindrical barrel 20a with an enclosed bottom and a cap 20b welded or otherwise attached to an open top of the barrel 20a that includes an outlet 22. A piston 20c is slidably positioned in the barrel 20a that is biased by a spring 20d to be seated in the outlet 22, thereby substantially sealing the interior of the barrel 20a. Optionally, the gas canister 20 may include one or more seals, e.g., for sealing the interior of the barrel 20a and/or sealing the recess 14 and/or fluid path 18 when the gas canister is mounted within the housing 12. For example, an o-ring 28 may provided around an exterior of the gas canister 20 for slidably engaging a wall of the recess 14, thereby providing a substantially fluid tight seal therebetween. In addition, an o-ring or other seal 20e may be provided on the piston 20c, e.g., to provide a substantially fluid tight seal between the piston 20c and the canister cap 20b when closed to prevent gas from escaping from the interior of the gas canister 20. Additional information regarding gas canisters that may be included in the device 10 may be found in U.S. Publication No. 2013/0345618, the entire disclosure of which is expressly incorporated by reference herein.

With continued reference to FIGS. 2 and 2A, an actuator pin 26 is located within the housing 12, e.g., within the recess 14 adjacent the outlet 22 of the gas canister 20, that includes a pin 26a extending from a head 26b. The pin 26a is oriented towards the gas canister 20 and has a smaller width than the outlet 22 such that the pin 26a enters the outlet 22 when the gas canister 20 is directed to the second position. This action may push the piston 20c out of the outlet 22 and allow gas in the barrel 20a to flow around the piston 20c and pin 26a and exit the outlet 22. The head 26b of the actuation pin 26 may include one or more passages 26c therethrough, thereby allowing the exiting gas to pass along the fluid path 18 into the syringe 60, as described elsewhere herein.

Returning to FIGS. 3-5, after delivery of gas from the gas canister 20, the cap 42 may be manipulated to return the actuator 40 to the outer position and the gas canister 20 to its first position. For example, the cap 42 may be rotated to thread the stem 44 away from the gas canister 20, and the bumper 24 may resiliently direct the gas canister 20 back to the first position shown in FIG. 3. Alternatively, if the actuator 40 is activated by depressing the cap 42, the cap 42 may simply be released, and the gas canister 20 may return to the first position due to the bias of the bumper 24. With the actuator 40 deactivated, the pin 26a is withdrawn from the outlet 22, allowing the piston 20c to reseal the outlet 22 and discontinue flow of gas.

In an alternative embodiment, the gas canister 20 may include a penetrable plenum, membrane, or other enclosure (e.g., instead of the piston 20c), and a needle or other puncturing element (not shown) may be provided in the recess 14 or fluid path 18 (e.g., instead of the actuation pin 26), which may be oriented to puncture the plenum on the outlet 22 when the gas canister 20 is directed to the second position. For example, upon activation of the actuator 40, the stem 44 may direct the gas canister 20 to the second position, thereby causing the puncturing element to penetrate the plenum and deliver pressurized gas from gas canister 20 into the fluid path 18 into the interior 66 of the syringe barrel 62. After delivery of gas from the gas canister 20, the cap 42 may be manipulated to return the actuator 40 to the outer position and the gas canister 20 to its first position, thereby withdrawing the puncturing element from the plenum, which may be configured to resiliently reseal itself and discontinue delivery of pressurized gas.

The filter 30 may be mounted within the housing 12 adjacent the actuation pin 26, e.g., a 0.20 or 0.22 micron filter to sterilize the gas exiting the gas canister 20 and/or remove contaminants from the fluid path 18.

Returning to FIG. 2, as shown the housing 12 may include a one or more pressure controllers, e.g., a pair of redundant flow restrictors 32 configured to limit and/or control the pressure of the gas leaving the gas canister 20 before being discharged into the syringe 60. In an exemplary embodiment, the flow restrictor(s) 32 may allow pressure to build within the fluid path 18 to a predetermined level, e.g., to limit the pressure of the pressurized gas introduced into the syringe 60 to no more than about 40 psi or otherwise appropriate to move the plunger 70 of the syringe 60 during filling. In addition, the restrictor(s) 32 may include flow resisting filter material that allows gas to bleed or vent to the outside atmosphere, e.g., through openings in the housing 12, when excessive pressure builds up within the fluid path 18, e.g., greater than about 40 psi or otherwise sufficient to move the plunger 70 of the syringe 60 during filling, as described elsewhere herein. Alternatively, other pressure relief mechanisms may be provided, such as a ball/spring pressure relief element (not shown) that opens when a predetermined pressure is reached within the fluid path 18.

Optionally, one or more seals may be provided in the recess 14, cavity 16, and/or fluid path 18 to substantially isolate the gas flowing from the gas canister 20 to the syringe 60 being filled and/or to prevent air or other contaminants from the entering the device 10. For example, as described above, an o-ring or other seal 28 may be provided around the gas canister 20, thereby sealing one end of the fluid path. In addition, as shown in FIG. 2, an elastomeric bumper or other seal 34 may be provided in the cavity 16 immediately adjacent the flow path 18. The seal 34 may provide a substantially fluid tight seal, e.g., when the syringe 60 is inserted into the cavity 16, which may minimize or eliminate leakage of gas from the fluid path 18 and/or may reduce the risk of contamination, e.g., of a needle 65a provided on the syringe 60.

During manufacturing and/or assembly, the housing 12 may be formed from one or more components that are molded, cast, machined and the like together, e.g., from plastic, metal, or composite materials. For example, the housing 12 may be molded from clamshell halves (not shown) in which passages are integrally molded corresponding to the recess 14, fluid path 18, and cavity 16. The components, e.g., the gas canister 20, bumper 24, actuation pin 26, filter 30, and pressure controller(s) 32 may be placed in their respective passages in a first of the clamshells and then a second clamshell (also including respective passages) may be placed over and attached to the first clamshell, thereby encasing the components therein. In exemplary embodiments, the housing clamshells may be substantially permanently attached together, e.g., by one or more of cooperating connectors (not shown), bonding with adhesive, sonic or heat welding, and the like, to provide the finished housing 12.

The actuator 40 and latch 50 may be formed, e.g., using one or more materials and/or methods similar to the housing 12, e.g., molded from plastic. The latch 50 may be coupled to the housing 12 adjacent the cavity, e.g., by engaging the hinge elements on the first end 52 of the latch and the housing 12 adjacent the opening 17. The stem 44 of the actuator 40 may be inserted into the housing 12 adjacent the gas canister 20 and the set screw 48 (or other connector) may be inserted into the housing 12 to secure the actuator 40 relative to the housing 12 yet allow desired movement.

The device 10 may be provided to a clinician or other user with a syringe 60 already inserted into and secured within the cavity 16 of the housing 12. Alternatively, the device 10 may be provided to the user without a syringe, e.g., such that the user may insert and fill a syringe of their choice (that is sized to be inserted into the cavity 16). For example, with the plunger 70 in its distal position, e.g., as shown in FIG. 2, the barrel 62 may be inserted into the opening 17 and cavity 16. Once fully inserted, the latch 50 may be directed to the engaged position, e.g., to engage the flanges 68 with the tabs 56 on the latch 50, and/or otherwise prevent movement and/or removal of the syringe 60. In either case, the final product may be sterilized and/or packaged as desired to the user who may prepare and use the syringe 60 during a medical procedure, e.g., a pneumatic retinopexy procedure.

Generally, as shown in FIGS. 3-6, the resulting device 10 (and optional syringe 60) may provide a single-use, disposable system that may facilitate fast and/or convenient transfer of gas from a high-pressure gas canister 20 into the syringe 60. For example, during use, if the device 10 is provided without a syringe, the user may select an appropriate syringe 60, fully depress the plunger 70 (e.g., as shown in FIG. 2), and insert the barrel 62 into the opening 17 and cavity 16 of the housing 12. Optionally, the user may attach a desired needle assembly 65 to the barrel 62 before inserting the syringe 60 into the cavity 16. Once fully seated, the latch 50 may be directed to the engaged position to secure the syringe 60 relative to the housing 12, thereby providing the device 10 and syringe 60 ready for a procedure, e.g., as shown in FIG. 3.

Turning to FIG. 4, the user may then activate the actuator 40, e.g., rotating and/or depressing the button 42 to direct the gas canister 20 to its second position, thereby opening the outlet 22 and delivering pressurized gas from the gas canister 20 along the fluid path 18 into the interior 66 of the syringe barrel 62. The pressure from the gas canister 20 may be limited by the controller(s) 32 yet sufficient to automatically cause the plunger 70 to move from a distal or fully depressed position to a proximal position as the interior 66 is filled with the pressurized gas, as shown in FIG. 5.

As can be seen in FIG. 1, the plunger 70 and latch 50 may include cooperating elements, e.g., recess 74 and groove 58, that may engage if the plunger 70 is pushed to a predetermined maximum fill volume, thereby preventing overfilling of the syringe 60 and/or accidental removal of the plunger 70 completely from the syringe 60.

Once the syringe 60 is filled, as shown in FIG. 6, the latch 50 may be flipped or otherwise directed to the disengaged position, and the syringe 60 may be removed from the cavity 16. The configuration of the cavity 16 and/or fluid path 18 may minimize exposure of the needle 65a, e.g., to reduce the risk of needle contamination.

Optionally, the actuator 40 may be manipulated to direct the gas canister 20 back to its first position and/or otherwise close the outlet 22 and discontinue delivery of gas from the gas canister 20. Alternatively, the actuator 40 may remain in its inner, activated position, and any residual gas remaining within the gas canister 20 may simply escape from the device 10, e.g., through the pressure controller(s) 32 and/or out the cavity 16.

The syringe 60 may then be used to deliver the pressurized gas therein to a patient, e.g., to insert the needle 65a into the patient's eye (not shown) and inject the gas during a pneumatic retinopexy procedure. After injection, the needle 65 may be withdrawn from the patient's eye, and then the syringe 60 and device 10 may be disposed of.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods do not rely on the particular order of steps set forth herein, the methods should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for performing a medical procedure, comprising:
    a housing comprising a recess, a syringe cavity sized for receiving a barrel of a syringe, and a fluid path extending between the recess and the syringe cavity;
    a source of pressurized gas contained entirely within the recess including an outlet communicating with the fluid path;
    a syringe comprising a barrel including a side wall reducing to a distal port on a distal end of the barrel communicating with an interior of the barrel and a plunger comprising a piston slidable within the interior of the barrel, the distal port and at least a portion of the side wall of the barrel of the syringe receivable in the syringe cavity in the housing such that the distal port communicates with the fluid path; and an actuator on the housing for selectively opening the outlet of the source of pressurized gas to deliver gas therein along the fluid path into the interior of the barrel, thereby causing the plunger to move from a distal position to a proximal position.

2. The system of claim 1, wherein the syringe comprises a needle extending from the distal port, the needle inserted into the syringe cavity and positioned within the fluid path when the syringe is received within the cavity.

3. The system of claim 2, wherein the needle is mounted on a needle assembly including a cap connected to the distal port by mating connectors.

4. The system of claim 1, wherein the syringe comprises a connector on the distal port, the system further comprising a needle comprising a mating connector connectable to the connector on the distal port for connecting the needle to the barrel.

5. The system of claim 1, wherein the source of pressurized gas comprises a single-dose gas canister.

6. The system of claim 5, wherein the gas canister has an internal volume of not more than about one milliliter (1 ml).

7. The system of claim 1, wherein the source of pressurized gas contains one of $SF_6$, $C_3F_8$, or $C_2F_6$.

8. The system of claim 1, further comprising a filter mounted within the housing in communication with the fluid path.

9. The system of claim 8, wherein the filter has a porosity to sterilize gas exiting from the source of pressurized gas before entering the interior of the barrel.

10. The system of claim 1, further comprising one or more pressure controllers mounted to the housing in communication with the fluid path.

11. The system of claim 10, wherein the one or more pressure controllers comprise a pressure regulator that limits pressure of the gas from the source of pressurized gas entering the interior of the barrel.

12. The system of claim 1, wherein the actuator comprises:
an actuation pin mounted in the housing adjacent the outlet; and
an actuator element extending outside the housing and configured to be manipulated to direct one of the actuation pin and the source of pressurized gas to cause the actuation pin to open the outlet and deliver gas along the fluid path into the interior of the barrel.

13. The system of claim 12, wherein the actuator element is movable from an outer position to an inner position to direct the source of pressurized gas towards the actuation pin to open the outlet.

14. The system of claim 13, wherein the actuator element comprises a cap that is rotatable relative to the housing to direct the actuator element from the outer position to the inner position.

15. The system of claim 13, wherein one of the actuator element and the source of pressurized gas is biased to direct the actuator element to the outer position.

16. The system of claim 12, wherein the source of pressurized gas comprises a gas canister including a piston substantially sealing the outlet, and wherein the actuation pin is configured to direct the piston away from the outlet to open the outlet.

17. The system of claim 1, further comprising one or more features on the housing and the syringe for releasably securing the syringe with the distal end of the barrel received in the cavity of the housing.

18. The system of claim 17, wherein the one or more features comprise a latch on the housing.

19. The system of claim 18, wherein the latch comprises a catch for limiting movement of the plunger beyond the proximal position.

20. The system of claim 1, wherein the housing comprises first and second opposite ends, wherein the actuator and the recess containing the source are located adjacent the first end, and wherein the syringe cavity is located adjacent the second end, the second end including an opening communicating with the syringe cavity such that a portion the barrel extends from the first end when the syringe is received through the opening into the syringe cavity.

21. A system for performing a medical procedure, comprising:
a housing comprising a recess therein carrying a source of pressurized gas including an outlet communicating with a fluid path extending from the outlet to a syringe cavity sized for receiving a barrel of a syringe;
a syringe comprising a barrel including a distal port on a distal end of the barrel communicating with an interior of the barrel and a plunger comprising a piston slidable within the interior of the barrel, the distal end of the barrel of the syringe receivable in the syringe cavity in the housing such that the distal port communicates with the fluid path; and
an actuator on the housing for selectively opening the outlet of the source of pressurized gas to deliver gas therein along the fluid path into the interior of the barrel, thereby causing the plunger to move from a distal position to a proximal position,
wherein the syringe comprises a needle extending from the distal port, the needle inserted into the syringe cavity and positioned within the fluid path when the syringe is received within the cavity, and
wherein the needle is mounted on an insert received in the distal port that at least partially fills an interior of the distal port.

22. A gas syringe filling device, comprising:
a housing defining a recess and a fluid path communicating from the recess with a cavity sized for receiving at least a portion of a barrel of a syringe therein;
a canister of pressurized gas contained entirely within the recess of the housing comprising an outlet communicating with the fluid path;
a filter contained within the housing in the fluid path; and
an actuator for selectively opening the outlet of the canister of pressurized gas to deliver gas therein along the fluid path into a barrel of a syringe received in the cavity.

23. The device of claim 22, wherein the actuator comprises:
an actuation pin mounted in the housing adjacent the outlet; and
an actuator element extending outside the housing and configured to be manipulated to direct one of the actuation pin and the canister within the housing to cause the actuation pin to open the outlet and deliver gas along the fluid path into an interior of the barrel.

24. The device of claim 23, wherein the canister is movably received within the recess, the actuator element configured to move the canister to engage the actuation pin to open the outlet.

25. A method for preparing a syringe, comprising:
providing a housing comprising a recess including a source of pressurized gas contained entirely within the recess, the housing comprising a fluid path communicating with an outlet of the source of pressurized gas and extending within the housing from the recess to a syringe cavity, the syringe comprising a barrel at least partially positioned in the syringe cavity such that a port of the barrel is in communication with the fluid path;
opening the outlet of the source of pressurized gas to deliver gas from the source of pressurized gas along the fluid path through the port into an interior of the barrel, thereby causing a plunger to move from a distal position to a proximal position; and
removing the barrel from the housing.

26. The method of claim 25, wherein the syringe is secured to the housing by one or more cooperating features on the syringe and the housing, and wherein removing the barrel comprises disengaging the one or more cooperating features to release the syringe after filling the syringe with pressurized gas.

27. The method of claim 26, wherein the one or more cooperating features comprise a latch on the housing that releasably engages one or more finger flanges of the syringe.

28. A system for performing a medical procedure, comprising:
an elongate housing comprising a first end, a second end, a recess therein carrying a gas canister contained entirely within the recess and containing pressurized gas including an outlet communicating with a fluid path, and a syringe cavity extending from an opening in the first end towards the second end;
a filter within the housing in the fluid path;
a syringe comprising a barrel including a distal end including a port communicating with an interior of the barrel and a plunger comprising a piston slidable within the interior of the barrel, the distal end and a distal portion of the barrel receivable through the opening into the syringe cavity in the housing such that the port communicates with the fluid path;
a latch for releasably securing the barrel proximal to the distal portion to secure the syringe to the housing with the distal end and distal portion in the syringe cavity; and
an actuator on the second end of the housing for selectively opening the outlet of the source of pressurized gas to deliver gas therein along the fluid path into the interior of the barrel, thereby causing the plunger to move from a distal position to a proximal position, the latch comprising a catch for limiting movement of the plunger beyond the proximal position.

29. The system of claim 28, wherein the syringe is received within the syringe cavity such that a proximal end of the barrel and the plunger extend from the first end of the housing, the latch engaging the proximal end of the barrel to secure the barrel to the housing.

* * * * *